United States Patent
Kroll et al.

(10) Patent No.: US 7,848,804 B1
(45) Date of Patent: Dec. 7, 2010

(54) APPARATUS AND RELATED METHODS FOR CAPACITOR REFORMING

(75) Inventors: Mark W. Kroll, Crystal Bay, MN (US); Vince Kapral, Redwood City, CA (US); Joseph Beauvais, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 688 days.

(21) Appl. No.: 11/764,664

(22) Filed: Jun. 18, 2007

(51) Int. Cl.
*A61N 1/39* (2006.01)

(52) U.S. Cl. .................. 607/5; 607/1; 607/2; 607/3; 607/4

(58) Field of Classification Search .................. None
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,712,555 A | 12/1987 | Thornander et al. | |
| 4,729,376 A | 3/1988 | DeCote, Jr. | |
| 4,788,980 A | 12/1988 | Mann et al. | |
| 4,809,697 A | 3/1989 | Causey, III et al. | |
| 4,940,052 A | 7/1990 | Mann et al. | |
| 4,944,298 A | 7/1990 | Sholder | |
| 4,944,299 A | 7/1990 | Silvian | |
| 4,969,467 A | 11/1990 | Callaghan et al. | |
| 5,350,410 A | 9/1994 | Kleks et al. | |
| 5,466,254 A | 11/1995 | Helland | |
| 5,476,483 A | 12/1995 | Bornzin et al. | |
| 5,573,550 A | 11/1996 | Zadeh et al. | |
| 5,685,315 A | 11/1997 | McClure et al. | |
| 5,861,006 A | 1/1999 | Kroll | |
| 5,899,923 A * | 5/1999 | Kroll et al. ..................... | 607/5 |
| 6,096,062 A | 8/2000 | Silvian | |
| 6,275,734 B1 | 8/2001 | McClure et al. | |
| 6,283,985 B1 | 9/2001 | Harguth et al. | |
| 6,706,059 B2 | 3/2004 | Harguth et al. | |
| 6,761,728 B2 | 7/2004 | Harguth et al. | |
| 2001/0047190 A1 | 11/2001 | Harguth et al. | |
| 2002/0095186 A1 | 7/2002 | Harguth et al. | |
| 2003/0088273 A1 | 5/2003 | Liu et al. | |
| 2004/0098058 A1 | 5/2004 | Harguth et al. | |
| 2004/0186520 A1 | 9/2004 | Harguth et al. | |
| 2004/0225327 A1 | 11/2004 | Norton et al. | |
| 2005/0027319 A1 | 2/2005 | Rossing | |

FOREIGN PATENT DOCUMENTS

| | | |
|---|---|---|
| WO | WO01/43149 | 6/2001 |
| WO | WO03/045497 | 6/2003 |
| WO | WO2004/102639 | 11/2004 |
| WO | WO2005/014109 | 2/2005 |

* cited by examiner

*Primary Examiner*—Carl H Layno
*Assistant Examiner*—Paula J Stice

(57) ABSTRACT

An apparatus and related methods for reforming a capacitor. One method includes charging the capacitor to a first voltage value, allowing the capacitor to self discharge, measuring a time it takes for the capacitor to self discharge to a second voltage value, and determining whether to reform the capacitor depending upon the measured self-discharge time.

13 Claims, 6 Drawing Sheets

APPARATUS AND RELATED METHODS FOR CAPACITOR REFORMING

FIELD OF THE INVENTION

The invention relates to the field of implantable medical devices ("IMDs"). More specifically, the invention relates to an apparatus and related methods for reforming capacitors within an IMD.

BACKGROUND

IMDs, e.g., pacemakers, cardioverters, and defibrillators, are adapted, i.e., configured, to be implanted within a patient's body and to generate therapeutic electrical stimulation, which can be applied to a patient's heart. Typically, an IMD includes signal generation circuitry for generating the therapeutic electrical stimulation, e.g., a therapeutic waveform or a shock, which is delivered to the heart via one or more body-implantable leads. Each of the leads includes one or more electrodes, which deliver the electrical stimulation from the IMD to the patient's heart and sense electrical signals that are output from the heart.

The IMD includes a microprocessor, which receives the electrical signals that are sensed from the patient's heart by the electrodes. The microprocessor also can induce the signal generation circuitry to generate the therapeutic electrical stimulation based on the electrical signals that are sensed from the heart. The IMD includes a memory, which is coupled to the microprocessor and stores instructions that control the operation of the IMD. Also, the IMD includes a battery, which is used to supply power to the IMD's electronics, and one or more capacitors, for example, aluminum electrolytic capacitors, which receive and store electrical charge from the battery. The electrical charge that is stored in the capacitors is used to create the therapeutic electrical stimulation that ultimately is delivered to the patient's heart.

An example of an IMD is an implantable cardioverter-defibrillator ("ICD"), which is capable of sensing when the patient's heart is experiencing particular forms of tachycardia that require cardioversion or defibrillation. For example, a typical ICD, in combination with its associated leads and electrodes, can sense when the atria or ventricles are fibrillating. After sensing the fibrillation, the ICD's microprocessor induces the signal generation circuitry to develop a high-voltage shock, e.g., a voltage between approximately 400 volts and approximately 1,000 volts, which is applied to the chamber of the heart that is fibrillating via the leads and electrodes.

During this process, electrical energy output from the battery initially is stored in the capacitor(s), and then is applied to the patient's heart. When the high-voltage electrical stimulation is delivered to the heart, it depolarizes the heart's cells in the chamber so that the cells can repolarize and function in a normal fashion. Accordingly, it is desirable that an ICD develops and provides the electrical stimulation very quickly following the detection of such a cardiac event.

A design constraint related to IMDs in general, and ICDs in particular, is that the amount of electrical charge that can be output from the battery is limited. Consequently, it is desirable to conserve the battery's electrical charge as much as possible because replacement of an IMD's battery involves an invasive surgical procedure. In an effort to conserve the battery's limited electrical charge, the IMD's capacitors are left uncharged unless the IMD's microprocessor determines that a cardiac event has been detected. However, leaving the capacitors uncharged for extended periods of time, e.g., for greater than approximately one week to four weeks, can result in degradation of the capacitors.

For example, a typical high-voltage capacitor that is used in an ICD has plates that are separated by an oxide dielectric material, which will degrade over time in the absence of a voltage being applied across the plates. If the capacitor's dielectric material has degraded, a subsequent charging of the capacitor can result in a considerable leakage current occurring between the capacitor's plates. The leakage current can prolong the time that it takes to charge the capacitor, and thereby delay the delivery of the therapeutic electrical stimulation to the patient's heart. A delay in the delivery of the therapeutic electrical stimulation to the patient's heart can result in disastrous consequences for the patient. Also, the larger the value of leakage current, the larger the amount of energy that must be expended to charge the capacitor to the desired charge level, and thus, can result in an increase in the consumption of battery power and a decrease in the longevity of the IMD.

A method that currently is used to deal with the problem of dielectric material degradation is to have the IMD periodically charge the capacitors, e.g., once every one to three months, and hold the capacitors at a predetermined high-voltage level for a period of time, e.g., a minute or so, before discharging the capacitors through a load internal to the IMD even if no cardiac event has been detected. This periodic charging of the capacitors is called "reforming the capacitors," and typically results in a rebuilding of the oxide layers within the dielectric material, which enables the capacitors to charge faster.

While the reformation process has the effect of reducing the degradation of the capacitor dielectric material, it does drain the battery, and thus, reduces the battery's longevity. Typically, the amount of charge that is required from the battery to reform an IMD's capacitor progressively increases over time. Thus, depending upon the age of the dielectric material, reforming the capacitors may result in the capacitors being charged before the capacitor's dielectric material has degraded to a point where the leakage current would present a problem. Consequently, while periodically reforming the capacitor may reduce degradation of the dielectric material and the associated leakage current, it accomplishes these goals at a significant cost in battery charge and IMD longevity. Finally, reforming the capacitor every few months does not adequately keep the capacitor at optimal performance because the time constant of degradation is on the order of a week.

It should, therefore, be appreciated that there is a need for an apparatus and a method for reforming IMD capacitors so that the leakage current is maintained within acceptable tolerances without requiring an excessive expenditure of battery power. The present invention satisfies this need as discussed below.

SUMMARY

Certain embodiments described herein include a method for determining when to reform a capacitor. The method includes charging the capacitor to a first voltage value, allowing the capacitor to self discharge, measuring a time it takes for the capacitor to self discharge to a second voltage value, and determining whether to reform the capacitor depending upon the measured self-discharge time.

In other, more detailed features of the invention, the step of determining whether to reform the capacitor depending upon the measured self-discharge time includes determining if the measured self-discharge time is greater than a first time period, and reforming the capacitor if the measured self-discharge time is not greater than the first time period. Also, the method can further include waiting for a second time period if the measured discharge time is greater than the first time period, and repeating the previous steps. In addition, the first voltage value can be approximately 20 volts, the second voltage value can be approximately 10 volts, the first time period can be approximately 5 seconds, and the second time period can be approximately 1 week.

In other, more detailed features of the invention, the method further includes providing a second capacitor, charging the second capacitor to the first voltage value, allowing the second capacitor to self discharge, measuring a time it takes for the second capacitor to self discharge to the second voltage value, determining if the measured self-discharge time for the second capacitor is greater than the first time period, and reforming the second capacitor if the measured self-discharge time for the second capacitor is not greater than the first time period. Also, the method can further include waiting for the second time period if the measured self-discharge time for the second capacitor is greater than the first time period, and repeating the previous steps.

Another exemplary method according to the invention is a method for reforming a capacitor. The method includes determining a value of leakage current for the capacitor, and applying a voltage to the capacitor that has a value that is mathematically determined based on the value of leakage current.

In other, more detailed features of the invention, the voltage that is applied to the capacitor has a value that is approximately equal to a maximum voltage rating for the capacitor multiplied by the value of leakage current divided by the sum of the value of leakage current and a predetermined current value. Also, the maximum voltage rating for the capacitor can be in a range from approximately 300 volts to approximately 700 volts, and the predetermined current value can be approximately 5 microamperes. In addition, the value of leakage current can be determined mathematically based on a capacitance value of the capacitor, and a measured change in a value of voltage across the capacitor over a period of time.

In other, more detailed features of the invention, the method includes determining if the value of leakage current is greater than a predetermined current value, ending the method before the step of applying the voltage to the capacitor if the value of leakage current is not greater than the predetermined current value, and performing the step of applying the voltage to the capacitor if the value of leakage current is greater than the predetermined current value. Also, the voltage can be applied to the capacitor for a period of time that is mathematically determined based on the value of leakage current. In addition, the predetermined current value can be 5 microamperes, and the period of time can be in a range from approximately 1 second to approximately 5 seconds or have a value equal to 5 seconds multiplied by the value of leakage current and divided by the sum of the value of leakage current and the predetermined current value. Furthermore, the method can include repeating previous steps.

An exemplary embodiment of the invention is an apparatus that is adapted to be included in an IMD having a battery, a microcontroller, and an electrode configuration switch. The apparatus is adapted to convert electrical energy from the battery into a voltage that is to be delivered to inputs of the electrode configuration switch. The apparatus includes a transformer, a first capacitor, a second capacitor, a first diode, a second diode, and a first switch. The transformer includes a first winding that is adapted to be coupled to the battery, a second winding, and a third winding. The first capacitor is coupled in series with the first diode, and the series-coupled first capacitor and first diode are coupled across the second winding. The second capacitor is coupled in series with the second diode, and the series-coupled second capacitor and second diode are coupled across the third winding. The first switch is coupled between a first node and a second node. The first node is between the first capacitor and the second winding, the second node is between the second capacitor and the second diode, and the first switch is adapted to be controlled by the microcontroller.

In other, more detailed features of the invention, the apparatus also includes a first output and a second switch. The first output is adapted to be coupled to a first input of the electrode configuration switch. The second switch is coupled between the first capacitor and the first output, and is adapted to be controlled by the microcontroller.

In other, more detailed features of the invention, the apparatus also includes a second output, a third switch, and a fourth switch. The second output is adapted to be coupled to a second input of the electrode configuration switch. The third switch is coupled between the second capacitor and the second output. The fourth switch is coupled between the first capacitor and the second output. The third and fourth switches are adapted to be controlled by the microcontroller.

In other, more detailed features of the invention, when the microcontroller is coupled to the apparatus, the first, second, third, and fourth switches are controlled by the microcontroller. The microcontroller can manipulate the first, second, third, and fourth switches to facilitate the application of a voltage across the first and second outputs. The voltage across the first and second outputs is selected from the group consisting of a first voltage across the first capacitor and a second voltage across a series coupling of the first capacitor and the second capacitor.

In other, more detailed features of the invention, the apparatus also includes an additional switch that is coupled to the first winding and also is adapted to be coupled to the battery. The additional switch is adapted to be controlled by the microcontroller. When the battery is coupled to the first winding and the additional switch is closed, the additional switch permits electrical energy from the battery to energize the transformer. In addition, the IMD can further include a voltage measuring circuit that is coupled to the microcontroller, and the microcontroller is adapted to determine a voltage across one of the first and second capacitors using the voltage measuring circuit.

Other features of the invention should become apparent from the following description of the preferred embodiments taken in conjunction with the accompanying drawings, which illustrate, by way of example, the principles of the invention.

DETAILED DESCRIPTION

Figure 1:
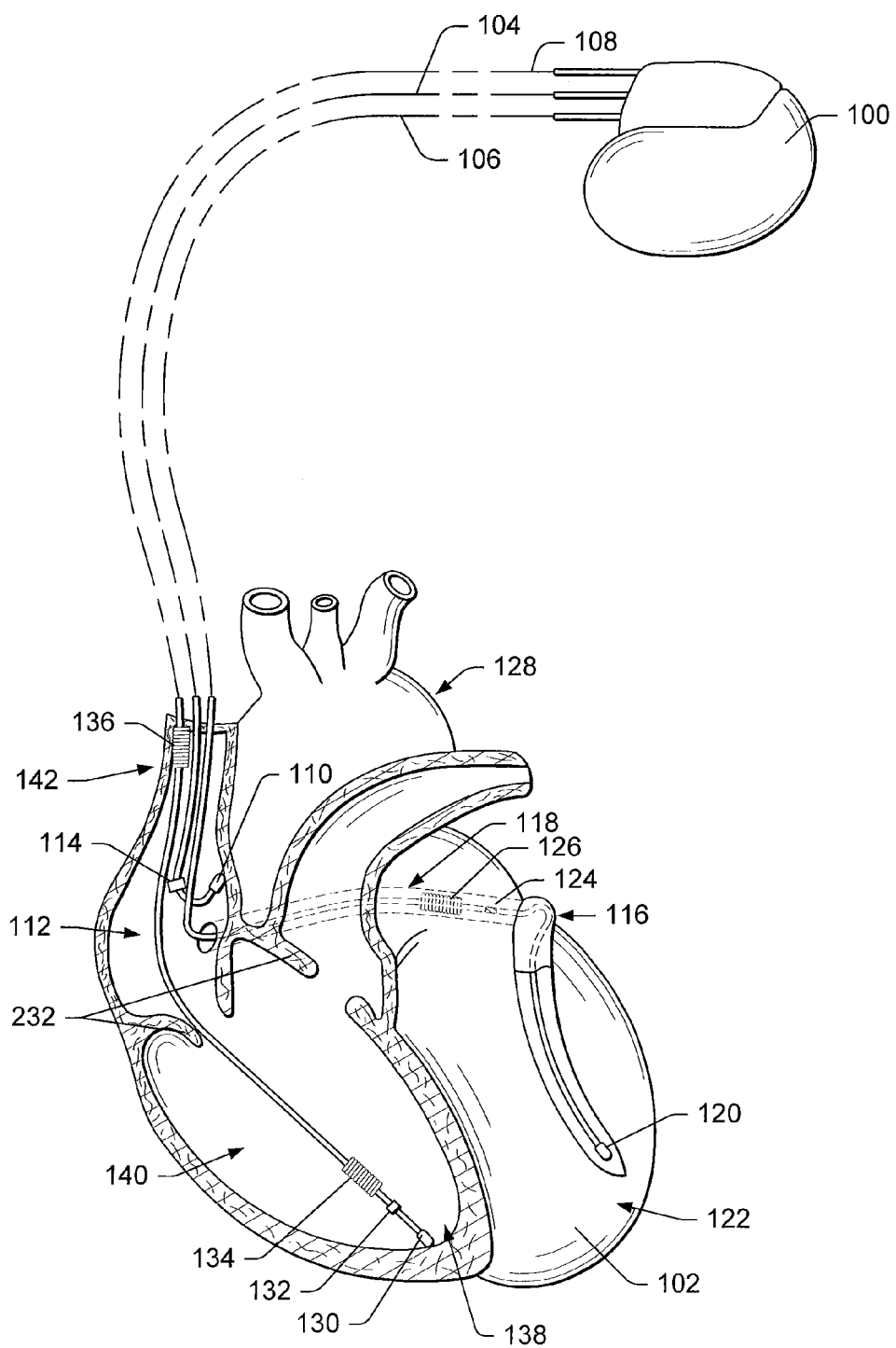
FIG. 1 is a simplified diagram illustrating an exemplary IMD embodying the present invention, which is coupled to three leads that are positioned within a patient's heart.

Although the invention can be used in conjunction with a wide variety of medical device, for example, IMDs, with reference now to the illustrative drawings, and particularly to FIG. 1, there is shown an exemplary IMD 100, a heart stimulation device, e.g., a pacemaker, a defibrillator, and/or a cardioverter, in electrical communication with a patient's heart 102 by way of three leads 104, 106, and 108, suitable for delivering multi-chamber stimulation and shock therapy. To sense atrial cardiac signals and to provide right atrial chamber stimulation therapy, the IMD is coupled to an implantable right atrial lead 104 having at least an atrial tip electrode 110, which typically is implanted in contact with the patient's right atrium 112. As shown in FIG. 1, the right atrial lead 104 also includes a right atrial ring electrode 114.

To sense left atrial and ventricular cardiac signals and to provide left chamber pacing therapy, the IMD 100 is coupled to a coronary sinus lead 106, which is designed for placement in the coronary sinus region 116 via the coronary sinus 118, and for positioning a distal electrode 120 adjacent to the left ventricle 122 and/or additional electrode(s) 124 and 126 adjacent to the left atrium 128. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 120, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, entitled "Coronary Sinus Lead with Atrial Sensing Capability" to Helland, which is incorporated by reference herein.

In FIG. 1, the IMD 100 also is shown in electrical communication with the patient's heart 102 by way of an implantable right ventricular lead 108 having, in this implementation, a right ventricular tip electrode 130, a right ventricular ring electrode 132, a right ventricular coil electrode 134, and a superior vena cava ("SVC") coil electrode 136. Typically, the right ventricular lead is transvenously inserted into the heart to place the right ventricular tip electrode in the right ventricular apex 138 so that the right ventricle coil electrode will be positioned in the right ventricle 140 and the SVC coil electrode will be positioned in the superior vena cava 142. Accordingly, the right ventricular lead is capable of sensing or receiving cardiac signals, and delivering stimulation in the form of pacing and shock therapy to the right ventricle.

Figure 2:
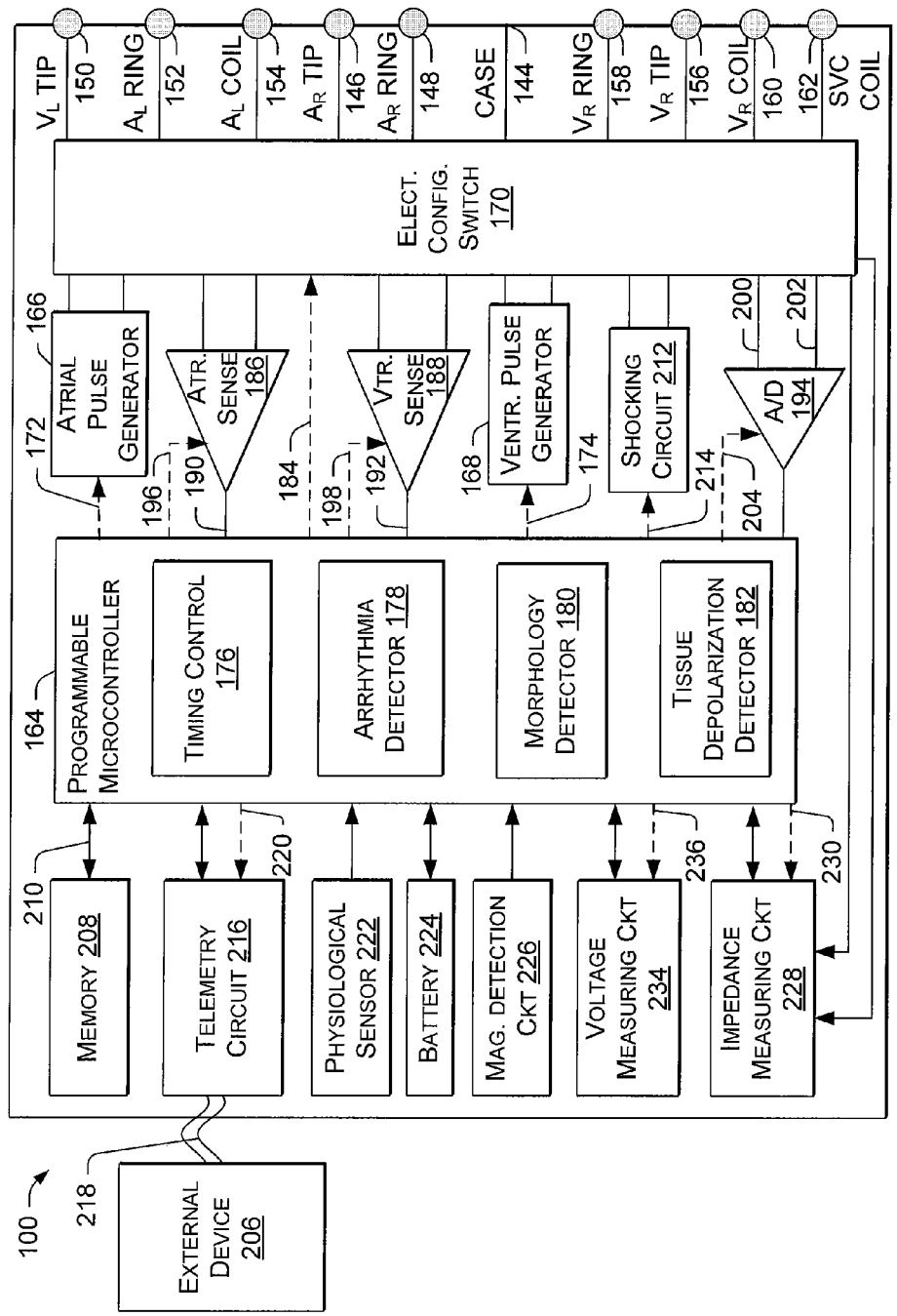
FIG. 2 is a functional block diagram of the exemplary IMD of FIG. 1.

FIG. 2 is an exemplary block diagram that depicts various components of the IMD 100 shown in FIG. 1. The IMD can be configured to treat both fast and slow arrhythmias with stimulation therapy, including cardioversion, defibrillation, and pacing stimulation. While a particular multi-chamber device is shown in FIG. 1, it is to be appreciated and understood that this is done for illustration purposes only. Thus, the techniques and methods described below can be implemented in connection with any suitably configured or configurable heart stimulation device. Accordingly, one having ordinary skill in the art could readily duplicate, eliminate, or disable the appropriate circuitry in any desired combination to provide a heart stimulation device that is capable of treating the appropriate chamber(s) 112, 122, 128, and 140 with cardioversion, defibrillation, and pacing stimulation.

The IMD 100 includes a housing 144, which often is referred to as the "can", "case", or "case electrode", and can be selected programmably to act as the return electrode for all "unipolar" modes of operation for the IMD. The housing can further be used as a return electrode alone, or in combination with one or more of the coil electrodes 126, 134 and 136 for shocking purposes. The housing further includes a connector (not shown) having a plurality of terminals 146-162 (shown schematically and, for convenience, the names of the electrodes to which they are connected are shown next to the terminals).

To achieve right atrial sensing and pacing, the connector (not shown) includes at least a right atrial tip terminal ("$A_R$ TIP") 146 adapted for coupling to the atrial tip electrode 110. As shown in FIG. 2, the block diagram also includes a right atrial ring terminal ("$A_R$ RING") 148 adapted for coupling to the atrial ring electrode 114. To achieve left chamber sensing, pacing, and shocking, the connector includes at least a left ventricular tip terminal ("$V_L$ TIP") 150, a left atrial ring terminal ("$A_L$ RING") 152, and a left atrial shocking terminal ("$A_L$ COIL") 154, which are adapted for coupling to the left ventricular tip electrode 120, the left atrial ring electrode 124, and the left atrial coil electrode 126, respectively.

To support right chamber sensing, pacing, and shocking, the connector (not shown) further includes a right ventricular tip terminal ("$V_R$ TIP") 156, a right ventricular ring terminal ("$V_R$ RING") 158, a right ventricular shocking terminal ("$V_R$ COIL") 160, and a superior vena cava shocking terminal ("SVC COIL") 162, which are adapted for coupling to the right ventricular tip electrode 130, the right ventricular ring electrode 132, the right ventricle coil electrode 134, and the SVC coil electrode 136, respectively.

The IMD 100 further includes a programmable microcontroller 164, i.e., a microprocessor-based control circuit, which controls the various modes of stimulation therapy. As is well known in the art, a microcontroller typically includes a microprocessor, or equivalent control circuitry, designed specifically for controlling the delivery of stimulation therapy, and can further include random access memory ("RAM") or read-only memory ("ROM"), logic and timing circuitry, state machine circuitry, and input/output ("I/O") circuitry. The microcontroller generally includes the ability to process or monitor input signals (data or information) as controlled by a program code stored in a designated block of memory. The type of microcontroller included in the IMD is not critical to the described implementations; hence, any suitable microcontroller can be used that carries out various functions such as those described herein. The use of microcontrollers for performing timing and data analysis functions are well known in the art.

Representative types of control circuitry that may be used in connection with the described embodiments can include the microprocessor-based control system of U.S. Pat. No. 4,940,052 to Mann et al., the state machine of U.S. Pat. No. 4,712,555 to Thornander et al., and U.S. Pat. No. 4,944,298 to Sholder, all of which are incorporated by reference herein. For a more detailed description of the various timing intervals used within the IMD 100 and their inter-relationship, see U.S. Pat. No. 4,788,980 to Mann et al., also incorporated by reference herein.

FIG. 2 also shows an atrial pulse generator 166 and a ventricular pulse generator 168, which are coupled to the microcontroller 164, and which generate pacing stimulation pulses for delivery by the right atrial lead 104, the coronary sinus lead 106, and/or the right ventricular lead 108 via an electrode configuration switch 170. It is understood that in order to provide stimulation therapy in each of the four chambers 112, 122, 128, and 140 of the heart 102, the atrial and the ventricular pulse generators can include dedicated, independent pulse generators, multiplexed pulse generators, or shared pulse generators. The atrial and ventricular pulse generators are controlled by the microcontroller via appropriate control signals 172 and 174, respectively, which trigger or inhibit the stimulation of pulses by the pulse generators.

The microcontroller 164 further includes timing control circuitry 176 that is configured to control the timing of the stimulation pulses, e.g., pacing rate, atrio-ventricular ("A-V") delay, inter-atrial conduction ("A-A") delay, or inter-ventricular conduction ("V-V") delay, etc., as well as to keep track of the timing of refractory periods, blanking intervals, noise detection windows, evoked response windows, alert intervals, marker channel timing, etc., which are well known in the art.

The microcontroller 164 can further include arrhythmia detector circuitry 178, morphology detector circuitry 180, and tissue depolarization detector circuitry 182. These components can be utilized by the IMD 100 when determining desirable times to administer various therapies. The components 178-182 can be implemented in hardware as part of the microcontroller, or as software/firmware instructions programmed into the IMD and executed by the microcontroller during certain modes of operation.

The electrode configuration switch 170 includes a plurality of switches for coupling the desired electrodes 110, 114, 120, 124, 126, and 130-136 to the appropriate I/O circuits, e.g., the atrial and ventricular pulse generators 166 and 168, respectively, thereby providing complete electrode programmability. Accordingly, the electrode configuration switch, in response to a control signal 184 from the microcontroller 164, determines the polarity of the stimulation pulses, e.g., unipolar, bipolar, combipolar, etc., by selectively closing the appropriate combination of switches, which are included in the electrode configuration switch, as is known in the art.

Atrial sensing circuits 186 and ventricular sensing circuits 188 also can be selectively coupled to the right atrial lead 104, the coronary sinus lead 106, and/or the right ventricular lead 108, through the electrode configuration switch 170 for detecting the presence of cardiac activity in each of the four chambers 112, 122, 128, and 140 of the heart 102. Accordingly, the atrial sensing circuit and the ventricular sensing circuit can include dedicated sense amplifiers, multiplexed amplifiers, or shared amplifiers. The electrode configuration switch determines the "sensing polarity" of the cardiac signal by selectively closing the appropriate switches, which are included in the electrode configuration switch, as is also known in the art. In this way, the medical practitioner can program the sensing polarity independent of the stimulation polarity. The sensing circuits, e.g., the atrial and ventricular sensing circuits, are optionally capable of obtaining information indicative of tissue depolarization.

Each atrial and ventricular sensing circuit 186 and 188, respectively, preferably employs one or more low-power, precision amplifiers with programmable gain and/or automatic gain control, bandpass filtering, and a threshold detection circuit, as is known in the art, to selectively sense the cardiac signal of interest. The automatic gain control enables the IMD 100 to deal effectively with the difficult problem of sensing the low-amplitude signal characteristics of atrial or ventricular fibrillation. For a complete description of a typical sensing circuit, the reader is directed to U.S. Pat. No. 5,573,550 ("the '550 patent"), entitled "Implantable Stimulation Device having a Low-Noise, Low-Power, Precision Amplifier for Amplifying Cardiac Signals" to Zadeh et al. For a complete description of an automatic gain control system, the reader is directed to U.S. Pat. No. 5,685,315 ("the '315 patent"), entitled "Cardiac Arrhythmia Detection System for an Implantable Stimulation Device" to McClure et al. Accordingly, the '550 and the '315 patents are hereby incorporated by reference herein.

The outputs 190 and 192 of the atrial and ventricular sensing circuits 186 and 188, respectively, are coupled to the microcontroller 164, which, in turn, is able to trigger or inhibit the atrial and ventricular pulse generators 166 and 168, respectively, in a demand fashion in response to the absence or presence of cardiac activity in the appropriate chambers 112, 122, 128, and 140 of the heart 102. Furthermore, the microcontroller is capable of analyzing information output from the atrial and ventricular sensing circuits, and/or an analog-to-digital ("A/D") data acquisition system 194 (the A/D data acquisition system is discussed below) to determine, or detect, whether, and to what degree, tissue depolarization has occurred in the heart and to program a pulse, or pulses, in response to such determinations. The atrial and ventricular sensing circuits, in turn, receive control signals over signal lines 196 and 198, respectively, from the microcontroller for purposes of controlling the gain, threshold, polarization charge removal circuitry (not shown), and timing of any blocking circuitry (not shown) that is coupled to the inputs of the atrial and ventricular sensing circuits, as is known in the art.

For arrhythmia detection, the IMD 100 utilizes the atrial and ventricular sensing circuits 186 and 188, respectively, which are coupled between the microcontroller 164 and the electrode configuration switch 170, and configured to sense cardiac signals and to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. Of course, a circuit can accomplish both sensing and detection simultaneously. In addition, such a circuit also can ascertain an event cycle length as well. The timing intervals between sensed events, e.g., P-waves, R-waves, and depolarization signals associated with fibrillation, are then classified by the arrhythmia detector 178 included in the microcontroller by, for example, comparing them to a predefined rate zone limit, i.e., bradycardia, normal, low-rate ventricular tachycardia ("VT"), high-rate VT, and fibrillation rate zones, and/or various other characteristics, e.g., sudden onset, stability, physiologic sensors, and morphology, etc. Such classification can aid in the determination of the type of remedial therapy that is needed, e.g., bradycardia pacing, anti-tachycardia pacing, cardioversion shocks or defibrillation shocks, collectively referred to as "tiered therapy". Optionally, an arrhythmia cycle length is ascertained during and/or after arrhythmia sensing and/or detection using the same and/or other components.

Cardiac signals are also applied to inputs 200 and 202 of the A/D data acquisition system 194, which is coupled between the microcontroller 164 and the electrode configuration switch 170. The A/D data acquisition system receives control signals over signal line 204 from the microcontroller.

The A/D data acquisition system is configured to acquire intracardiac electrogram signals, to convert the raw analog data into a digital signal, and/or to store the digital signals for later processing and/or telemetric transmission to an external device 206, e.g., a programmer, transtelephonic transceiver, or a diagnostic system analyzer, (hereinafter referred to as a "programmer") which is configured to be operated by the medical practitioner, and to communicate with the IMD 100. The A/D data acquisition system is coupled to the right atrial lead 104, the coronary sinus lead 106, and the right ventricular lead 108 through the electrode configuration switch to sample cardiac signals across any pair of desired electrodes 110, 114, 120, 124, 126, and 130-136.

Advantageously, the A/D data acquisition system 194, or other system or circuitry, e.g., the atrial sensing circuit 186 and the ventricular sensing circuit 188, can be coupled to the microcontroller 164, or other detection circuitry, for analyzing the obtained information to detect an evoked response from the heart 102 in response to an applied stimulus, thereby aiding in the detection of local tissue depolarization and/or global tissue depolarization, i.e., "capture." Global tissue depolarization or capture generally corresponds with contraction of cardiac tissue. For example, the microcontroller is capable of analyzing obtained information to detect a depolarization signal during a window following a stimulation pulse, the presence of which typically indicates that some degree of tissue depolarization has occurred. In one implementation, the microcontroller enables depolarization detection by triggering the ventricular pulse generator to generate a stimulation pulse, starting a depolarization detection window using the timing control circuitry within the microcontroller, and enabling the data acquisition system via a control signal over signal line 204 to sample the cardiac signal that falls in the depolarization detection window. The information obtained through the data acquisition system is then analyzed to determine whether and/or to what degree tissue depolarization has occurred. This analysis optionally uses signal amplitude, gradient, integral, etc. to ascertain whether tissue activation has occurred and, if so, to ascertain a corresponding activation time or times. Such results are useful in determining, for example, pacing pulse regimens and/or whether to administer cardioversion level stimuli.

To facilitate detection of tissue depolarization, the microcontroller 164 includes a dedicated tissue depolarization detector 182, implemented in hardware and/or software. The tissue depolarization detector is capable of analyzing information obtained through the atrial and ventricular sensing circuits 186 and 188, respectively, and/or the A/D data acquisition system 194. The tissue depolarization detector analyzes the sensed information to produce a result, such as, activation time. Of course, the tissue depolarization detector is also capable of noting whether activation has occurred during any given time period. The tissue depolarization detector or other microprocessor features can use these results to determine pacing pulse regimens and/or other actions. As described herein, the tissue depolarization detector optionally detects local and/or global depolarization.

The implementation of tissue depolarization detection circuitry 182 and algorithms are well known. See, for example, U.S. Pat. Nos. 4,729,376 and 4,708,142 to Decote, Jr.; U.S. Pat. No. 4,686,988 to Sholder; U.S. Pat. No. 4,969,467 to Callaghan et al.; and U.S. Pat. No. 5,350,410 to Kleks et al.; all of which are hereby incorporated by reference herein. The type of depolarization detection system used is not critical to the described implementations.

The microcontroller 164 is further coupled to a memory 208 by a suitable data/address bus 210, wherein the programmable operating parameters used by the microcontroller are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, and vector of each shocking pulse to be delivered to the patient's heart 102 within each respective tier of therapy. One feature of the described embodiments is the ability to sense and store a relatively large amount of data, e.g., from the A/D data acquisition system 194, which data can then be used for subsequent analysis to guide the programming of the device.

In the case where the IMD 100 is intended to operate as an implantable cardioverter/defibrillator ("ICD") device, the IMD detects the occurrence of an arrhythmia and automatically applies an appropriate therapy to the heart 102, or is aimed at terminating the detected arrhythmia. Various exemplary methods of ICD operation are described below. According to various methods, the microcontroller 164 controls a shocking circuit 212, which is coupled between the microcontroller and the electrode configuration switch 170, and receives control signals over signal line 214. The shocking circuit generates shocking pulses of low energy (up to approximately 0.5 J), moderate energy (from approximately 0.5 J to approximately 10 J), or high energy (from approximately 11 J to approximately 40 J), as controlled by the microcontroller. Such shocking pulses are typically applied to the patient's heart through at least two shocking electrodes, e.g., the left atrial coil electrode 126, the right ventricular coil electrode 134, and/or the SVC coil electrode 136. As noted above, the housing 144 can act as an active electrode in combination with the right ventricular tip electrode 130, or as part of a split electrical vector using the SVC coil electrode or the left atrial coil electrode, i.e., using the right ventricular tip electrode as a common electrode.

Cardioversion level shocks are generally considered to be of a low to moderate energy level, so as to minimize pain felt by the patient, and/or synchronized with an R-wave and/or pertaining to the treatment of tachycardia. Defibrillation shocks are generally of moderate to high energy level, i.e., corresponding to thresholds in the range from approximately 5 J to approximately 40 J, delivered asynchronously, since R-waves may be too disorganized, and pertaining exclusively to the treatment of fibrillation. Accordingly, the microcontroller 164 is capable of controlling the synchronous or asynchronous delivery of the shocking pulses. The term "cardioversion level" and/or "cardioversion", as used herein, include shocks having low, moderate, and high energy levels, i.e., cardioversion level shocks and defibrillation shocks.

Advantageously, the operating parameters of the IMD 100 can be non-invasively programmed into the memory 208 through a telemetry circuit 216 in telemetric communication via communication link 218 with the programmer 206. The microcontroller 164, which is coupled to the telemetry circuit, activates the telemetry circuit with a control signal 220. The telemetry circuit advantageously allows intracardiac electrograms ("ECGs") and status information relating to the operation of the IMD, as contained in the microcontroller or memory, to be sent to the programmer through the communication link. For examples of such devices, see U.S. Pat. No. 4,809,697, entitled "Interactive Programming and Diagnostic System for use with Implantable Pacemaker" to Causey, Ill. et al.; U.S. Pat. No. 4,944,299, entitled "High Speed Digital Telemetry System for Implantable Device" to Silvian; and U.S. Pat. No. 6,275,734, entitled "Efficient Generation of Sensing Signals in an Implantable Medical Device such as a Pacemaker or ICD" to McClure et al., which patents are incorporated by reference herein.

The IMD 100 can further include a physiological sensor 222, commonly referred to as a "rate-responsive" sensor because it typically is used to adjust the pacing stimulation rate output from the IMD according to the exercise state of the patient. The physiological sensor can be used to detect changes in cardiac output, changes in the physiological condition of the heart 102, or diurnal changes in activity, e.g., detecting sleep and wake states of the patient. The microcontroller 164 is coupled to the physiological sensor, receives the output of the physiological sensor, and responds by adjusting the various pacing parameters, e.g., rate, A-V Delay, V-V Delay, etc., at which the atrial and ventricular pulse generators 166 and 168, respectively, generate stimulation pulses.

While shown as being included within the IMD 100, it is to be understood that the physiologic sensor 222 also can be external to the IMD, yet still be implanted within, or carried by, the patient. Examples of physiologic sensors that can be implemented in the IMD include known sensors that, for example, sense respiration rate, pH of blood, ventricular gradient, and so forth. Another sensor that can be used is one that detects activity variance, wherein an activity sensor is monitored diurnally to detect the low variance in the measurement corresponding to the sleep state. An example of an activity sensor is an accelerometer, e.g., a piezoelectric crystal, which is mounted within the housing 144 of the IMD. However, any sensor can be used that is capable of sensing a physiological parameter that corresponds to the exercise state of the patient. For a complete description of the activity variance sensor, the reader is directed to U.S. Pat. No. 5,476,483 to Bornzin et al., which patent is hereby incorporated by reference.

More specifically, the physiological sensor 222 optionally includes sensors for detecting movement, position, and/or minute ventilation ("MV") in the patient. Minute ventilation is defined as the total volume of air that moves in and out of a patient's lungs in a minute. During use, electrical signals generated by a position sensor and an MV sensor are sent to the microcontroller 164 for analysis in determining whether to adjust the pacing rate, etc. Optionally, the microcontroller monitors the signals for indications of the patient's position and activity status, such as whether the patient is climbing or descending a flight of stairs, or whether the patient is sitting up after lying down.

The IMD 100 additionally includes a battery 224, which is coupled to the microcontroller 164 and is configured to provide electrical power to all of the IMD circuits shown in FIG. 2. For the IMD, which, in this example, employs shocking therapy, the battery is capable of operating at low current drains, e.g., preferably less than 10 µA, for long periods of time and is capable of providing high-current pulses for capacitor charging when the patient requires a shock pulse, e.g., preferably, in excess of 2 A, at voltages above 2 V, for periods of 10 seconds or more.

The IMD 100 can further include magnet detection circuitry 226, which is coupled to the microcontroller 164, and configured to detect when a magnet (not shown) is placed over the IMD. The magnet can be used by the medical practitioner to perform various tests of the IMD and/or to signal the microcontroller that the programmer 206 is in place to receive data from, or transmit data to, the microcontroller through the telemetry circuit 216.

The IMD 100 further includes an impedance measuring circuit 228, which is coupled to the microcontroller 164 and which is enabled by the microcontroller via a control signal 230. The known uses for an impedance measuring circuit include, but are not limited to, lead impedance surveillance during the acute and chronic phases for proper lead positioning or dislodgement; detecting operable electrodes 110, 114, 120, 124, 126, and 130-136 and automatically switching to an operable pair of electrodes if dislodgement occurs; measuring respiration or minute ventilation; measuring thoracic impedance for determining shock thresholds; detecting when the IMD has been implanted; measuring stroke volume; and detecting the opening of heart valves 232, etc. Advantageously, the impedance measuring circuit is coupled to the electrode configuration switch 170 so that any desired electrode can be coupled to the impedance measuring circuit.

The IMD 100 also includes a voltage measuring circuit 234, which is coupled to the microcontroller, is enabled by the microcontroller 164 via a control signal 236, and is configured to measure the voltage output across various of the IMD's components and the electrodes 110, 114, 120, 124, 126, and 130-136. More specifically, the voltage measuring circuit can be used by the microcontroller to measure voltages that are input to the microcontroller, e.g., voltages from the atrial sensing circuit 186, the ventricular sensing circuit 188, and the A/D acquisition system 194.

Figure 3:
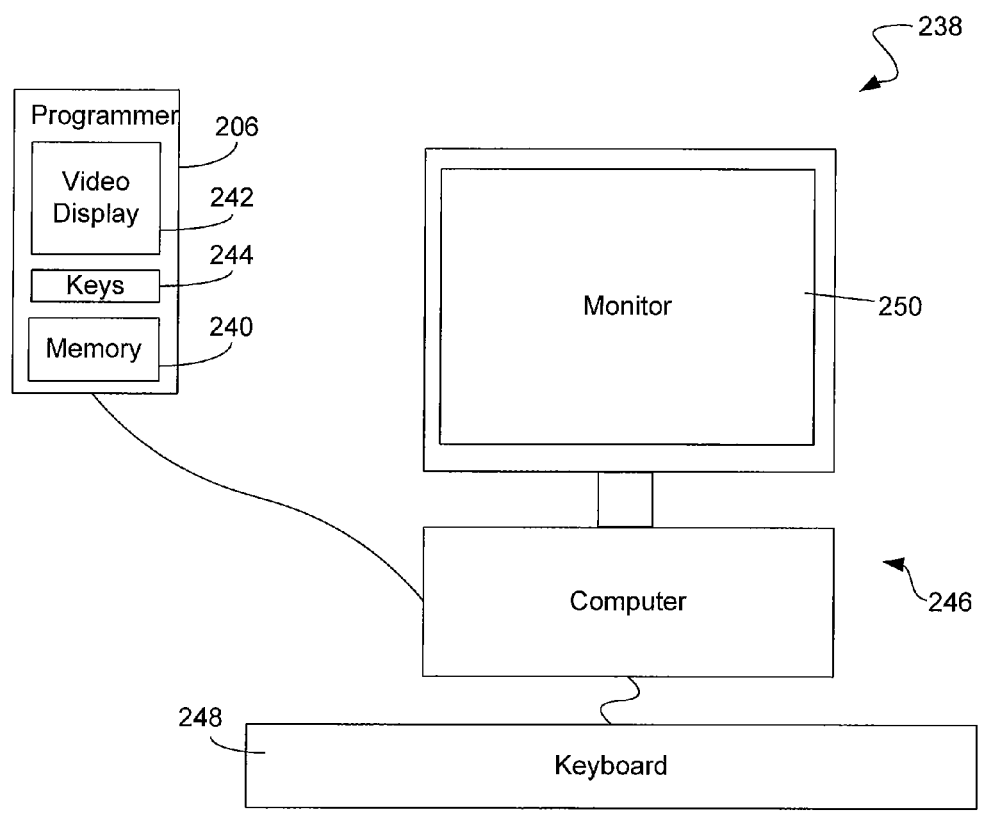
FIG. 3 is a simplified diagram illustrating an exemplary programmer control system, which is configured to communicate with the IMD of FIG. 1.

Referring additionally to FIG. 3, the programmer 206, which can be, for example, a telemetry wand or another type of communication device for wireless communication with the IMD 100, is included as part of a programmer control system 238, which is configured to communicate with the IMD. The programmer includes a programmer memory 240, which is used for storing the software used to operate the programmer, for data processing, and for long-term data storage. The programmer memory can include any type of memory suitable for long-term data storage, e.g., a RAM, a ROM, an EEPROM, a flash memory, a compact disc read-only memory ("CDROM"), a digital video disc ("DVD"), a magnetic cassette, a magnetic tape, a magnetic disc drive, a rewritable optical disk, or any other medium that can be used to store information. The programmer also can include an output device 242, e.g., a video display and/or a touch screen, which is configured to display data transmitted from the IMD to the programmer; and an input device 244, e.g., keys and/or buttons, which is configured to receive input from the medical practitioner.

The programmer control system 238 also includes a personal computer 246, which is coupled to the programmer 206, and controls the electrical operation of the programmer. In addition, the programmer control system includes a user input device 248, e.g., a keyboard, a pen, and/or a voice interface. Through the user input device, the medical practitioner can issue commands to the IMD 100 when the programmer is in communication with the IMD. The programmer control system also includes a user output device 250, e.g., a monitor and/or a printer, which is coupled to the programmer and used to display the status of the IMD and/or data transmitted from the IMD to the programmer.

The medical practitioner can use the user input device 248 to prompt the transmission of information from the programmer 206 to the IMD 100, which can include IMD programming commands and interrogation commands. In response to an interrogation command transmitted from the programmer to the IMD, a wide variety of real time and stored data that is particular to the patient and to the status of the IMD can be transmitted telemetrically by the IMD, via the telemetry circuit 216, to the programmer. Also, the data transmitted from the IMD to the programmer can include information related to currently programmed IMD operating modes and parameter values, the identification ("ID") of the IMD, the patient's ID, the IMD's implantation date, the programming history of the IMD, real time event markers, and the like.

Figure 4:
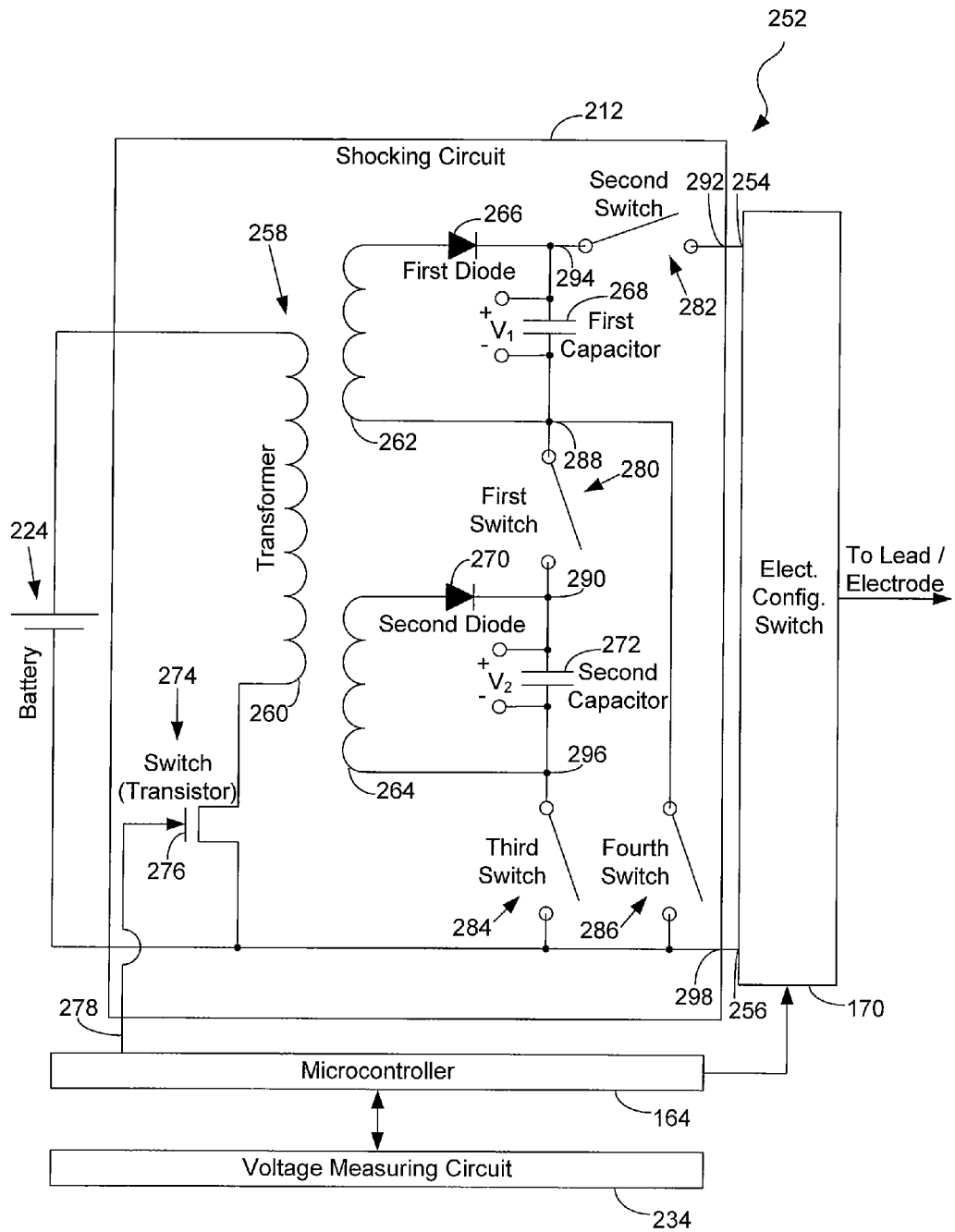
FIG. 4 is a functional block diagram that includes a schematic diagram of an exemplary apparatus according to the present invention that is included as part of the IMD of FIG. 1.

According to embodiments of the present invention, the IMD 100 that is shown in FIGS. 1 and 2 includes the apparatus 252 shown in FIG. 4 as part of the IMD's shocking circuit 212. The apparatus, which is configured to convert electrical energy from the battery 224 into a voltage that is delivered to a first input 254 and a second input 256 of the electrode configuration switch 170, includes a transformer 258 having a first winding 260, a second winding 262, and a third winding 264. The first winding is configured to be coupled to the battery. The second winding is coupled in parallel across a first diode 266 and a first capacitor 268 that are coupled together in series. Similarly, the third winding is coupled in parallel across a second diode 270 and a second capacitor 272 that are coupled together in series.

A switch 274, e.g., a transistor, is coupled to the transformer's first winding 260 so that actuation of the transistor results in the battery 224 energizing the first winding of the transformer 258. As shown in FIG. 4, the gate 276 of the transistor is coupled to the IMD's microcontroller 164 via a control line 278. Thus, the microcontroller can control when, and for how long, the first winding is energized with electrical current from the battery by sending an appropriate signal on the control line to the gate of the transistor.

After fully energizing the transformer's first winding 260, switch 274 is turned off, which results in the transformer's second and third windings 262 and 264, respectively, passing current through the rectifying diodes, i.e., the first and second diodes 266 and 270, respectively, and into the first and second capacitors 268 and 272, respectively. In this manner, the first and second capacitors are charged as a result of the microcontroller 164 turning on and off the transistor 274. The capacitor charging process is halted once the microcontroller stops cycling the transistor. By controlling the length of time the transistor is cycled on and off, the microcontroller can control the amount of charge that is stored in the first and second capacitors, and thus, can control the voltages $V_1$ and $V_2$ that are created across the first capacitor and second capacitor, respectively. The microcontroller can determine the values of $V_1$ and $V_2$ using the IMD's voltage measuring circuit 234.

The exemplary apparatus 252 shown in FIG. 4 also includes a first switch 280, a second switch 282, a third switch 284, and a fourth switch 286. The first switch is coupled between a first node 288 that is located between the second winding 262 and the first capacitor 268, and a second node 290 that is located between the second diode 270 and the second capacitor 272. The second switch is coupled between a first output 292 of the apparatus, which is configured to be coupled to the first input 254 of the electrode configuration switch 170, and a third node 294 that is located between the first diode 266 and the first capacitor. The third switch is coupled between a fourth node 296 that is located between the third winding 264 and the second capacitor 272 and a second output 298 of the apparatus, which is configured to be coupled to the second input 256 of the electrode configuration switch. The fourth switch is coupled between the first node and the second output. Each of the first, second, third, and fourth switches can be opened and closed independent of one another under the control of the microcontroller.

Because the four switches 280-286 can be opened and closed independent of one another, the microcontroller 164 can charge the first and second capacitors 268 and 272, respectively, in various configurations. During regular use, the first, second, and third switches 280, 282, and 284, respectively are closed and the fourth switch 286 is open, thus, resulting in the first capacitor being coupled in series with the second capacitor, and the combination of the first and second capacitors being coupled across the first and second outputs 292 and 298, respectively, of the apparatus 252. Thus, in this configuration, the series combination of the first and second capacitors can provide electrical charge to the electrode configuration switch 170, which, in turn, couples the charge into patient's heart 102 via the leads 104-106 and electrodes 110, 114, 120, 124, 126, and 130-136.

In another configuration, the apparatus 252 shown in FIG. 4 can deliver electrical charge from only the first capacitor 268 to the electrode configuration switch 170. This is accomplished by opening the first switch 280 and closing the second and fourth switches 282 and 286, respectively. In this configuration, only charge that is stored in the first capacitor will be coupled into the electrode configuration switch. Accordingly, the apparatus can output a multi-step voltage waveform depending upon which of the four switches 280-286 are closed.

In other configurations, each of the first and second capacitors 268 and 272, respectively, can be tested individually. In particular, when it is desired to test the operation of the first capacitor, e.g., measure the voltage $V_1$ across the first capacitor using the voltage measuring circuit 234, and/or test the operation of the second capacitor, e.g., measure the voltage $V_2$ across the second capacitor using the voltage measuring circuit, the microcontroller 164 can open the first switch 280 while cycling the transistor 274. In this manner, each of the first and second capacitors can be tested individually when the first switch is open.

As previously noted, during use, the microcontroller 164 is coupled to one or more electrodes 110, 114, 120, 124, 126, and 130-136 that sense electrical signals generated by the patient's heart 102. The microcontroller, upon receiving an electrical signal from one or more of the electrodes that indicates the occurrence of a cardiac event, sends a signal on the control line 278 so that the transistor 274 is pulsed on thereby energizing the first, second, and third windings 260, 262, and 264, respectively, of the transformer 258. This results in the transformer charging the first and second capacitors 268 and 272, respectively, to a first and second voltage $V_1$ and $V_2$, respectively. The desired values of $V_1$ and $V_2$ may vary depending upon the configuration of the IMD 100 and the type of cardiac event that is experienced by the patient. For example, if the IMD is adapted to correct ventricular fibrillation, the first and second capacitors both may be charged to approximately 800 volts. Subsequently, the electrical charge that is stored in the first and second capacitors is provided to the leads 104-108 via the electrode configuration switch 170 so that electrical stimulation can be delivered to the patient's heart.

It is desirable that the therapeutic electrical stimulation be delivered to the patient's heart 102 as soon as possible after the microcontroller 164 has detected the occurrence of a cardiac event, such as ventricular fibrillation. If the first and second capacitors 268 and 272, respectively, have not been charged for an extended period of time, there may be substantial leakage current through the dielectric material in the capacitors when the capacitors. This leakage current can result in the first capacitor and/or the second capacitor being charged over a longer of a period of time, and thus, delay the delivery of the electrical stimulation to the patient's heart.

Figure 5:
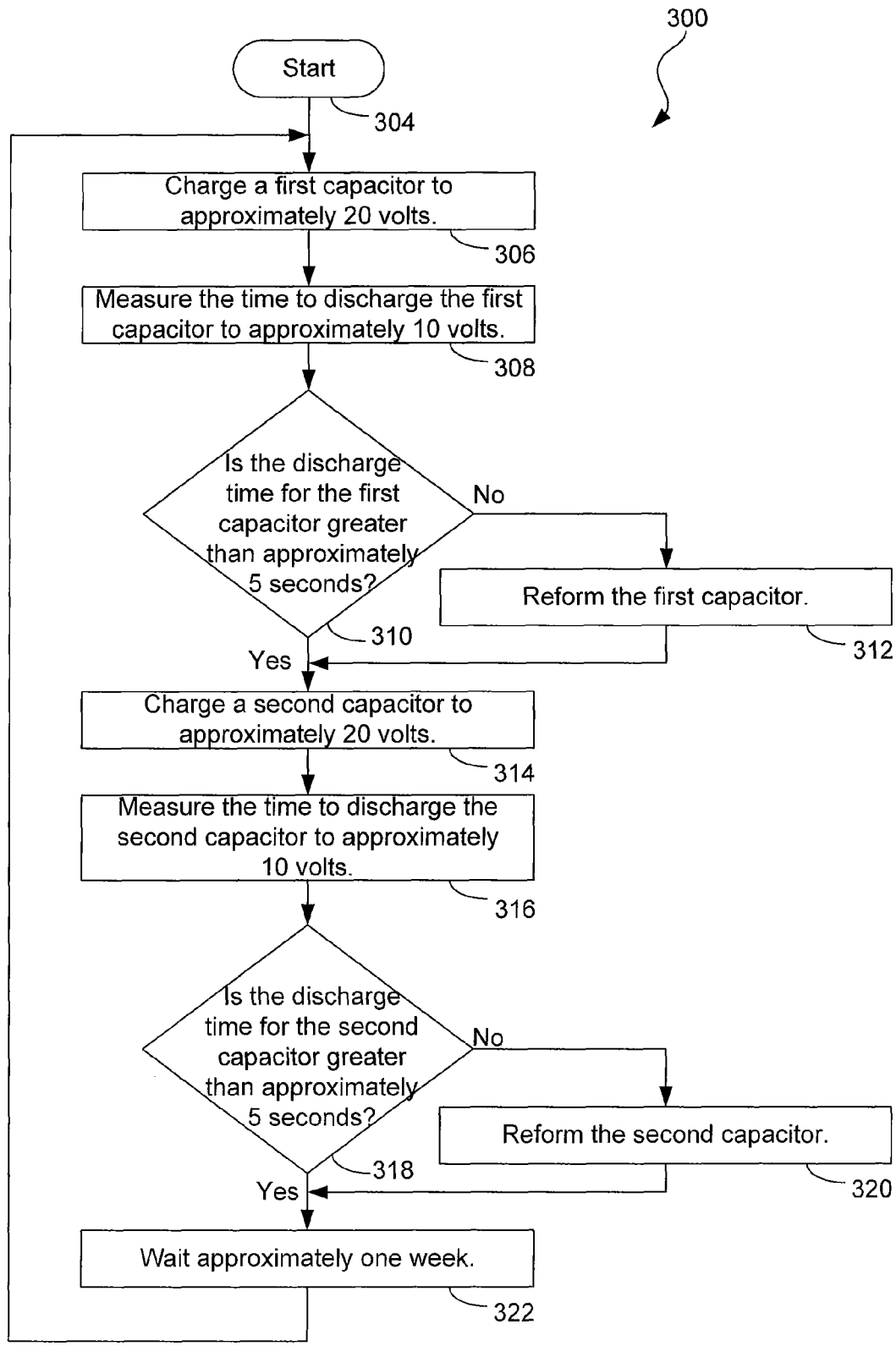
FIG. 5 is a flow diagram of an example algorithm for determining when to reform IMD capacitors according to the present invention, which can be implemented by the IMD of FIG. 1.
Figure 6:
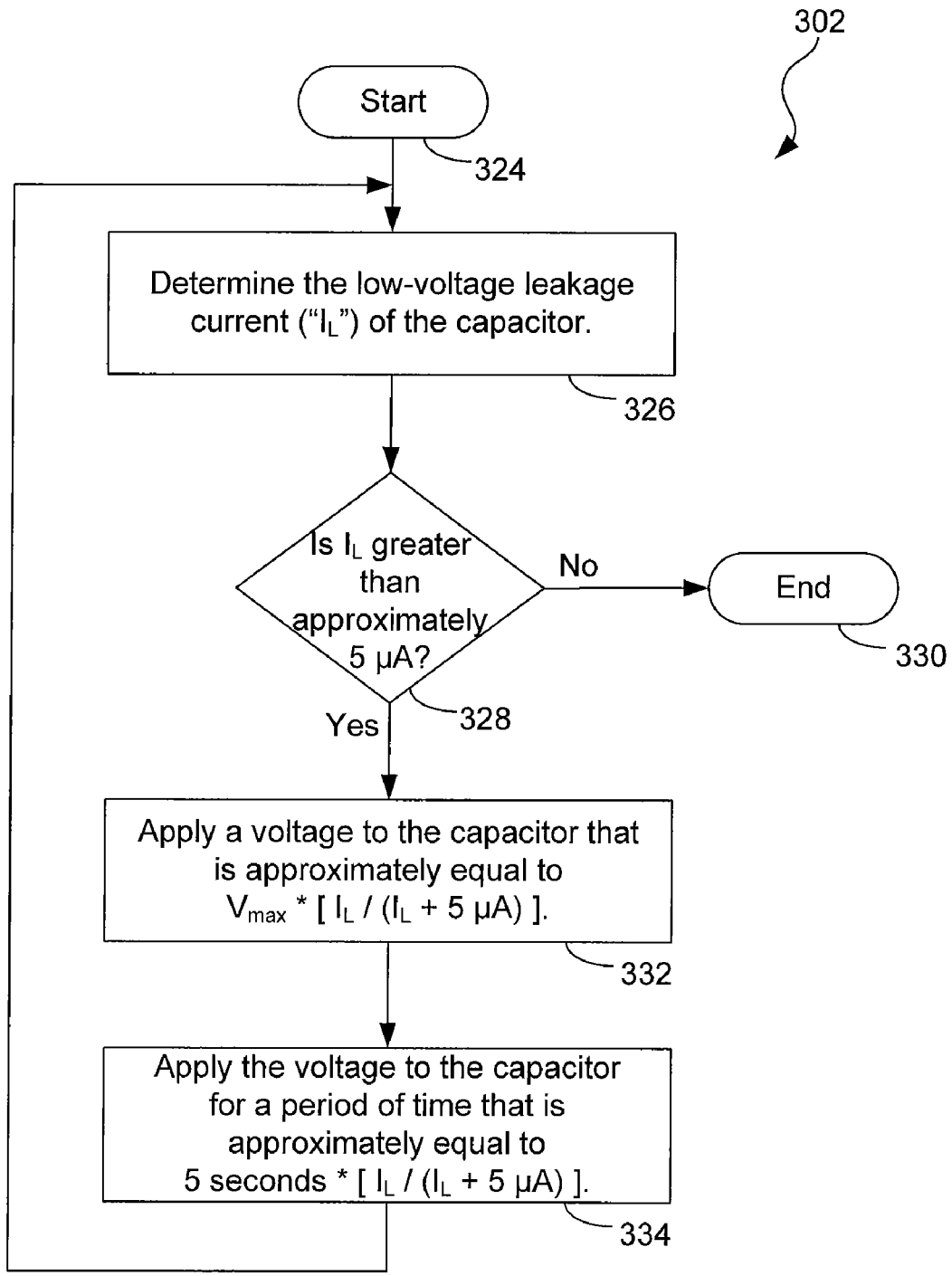
FIG. 6 is a flow diagram of another example algorithm for reforming IMD capacitors according to the present invention, which can be implemented by the IMD of FIG. 1.

FIGS. 5 and 6 include exemplary flowcharts of capacitor maintenance algorithms 300 and 302, respectively, according to the present invention that can be stored in program form in the IMD's memory 208 and implemented by the microcontroller 164. The capacitor maintenance algorithms can be initiated automatically by the microcontroller. Alternatively, the capacitor maintenance algorithms can be triggered manually by the medical practitioner using the programmer 206 alone or using the programmer in combination with the rest of the programmer control system 238. The purpose of the capacitor maintenance algorithms shown in FIGS. 5 and 6 is to ensure that the first and second capacitors 268 and 272, respectively, will be maintained in a condition where each capacitor's leakage current is kept within an acceptable range.

In one embodiment, the microcontroller 164 periodically, e.g., once a week, charges the first and second capacitors 268 and 272, respectively, using the apparatus 252 to a first low voltage value and decides whether one or both of the capacitors should be reformed based on how long it takes the voltage across each capacitor to drop to a second voltage value through self-discharge, i.e., dissipation of the capacitor's charge through leakage current. For example, in the example algorithm 300 shown in FIG. 5, the algorithm starts at step 304. Next, at step 306, the first capacitor is charged to a first voltage value equal to approximately 20 volts. At step 308, the microcontroller using the timing control circuitry 176 measures the time it takes for the voltage $V_1$ across the first capacitor, which is measuring using the voltage measuring circuit 234, to self discharge from the first voltage value of approximately 20 volts to a second voltage value of approximately 10 volts. Next, the microcontroller determines if the measured self-discharge time is greater than a first time period, e.g., approximately 5 seconds, at step 310. If the measured self-discharge time is not greater than approximately 5 seconds, then, at step 312, the microcontroller initiates the reformation of the first capacitor followed by step 314, which is discussed below. Thus, the microcontroller determines whether the first capacitor should be reformed depending upon the measured self-discharge time for the first capacitor.

If the measured time is greater than approximately 5 seconds, then the next step of the algorithm 300 is step 314 where the microcontroller 164 charges the second capacitor 272 to the first voltage value of approximately 20 volts. Next, at step 316, the microcontroller measures the time it takes the voltage $V_2$ across the second capacitor to self-discharge from the first voltage value of approximately 20 volts to the second voltage value of approximately 10 volts. At step 318, the microcontroller determines if the self-discharge time for the second capacitor is greater than the first time period of approximately 5 seconds. If the self-discharge time is not greater than approximately 5 seconds, then the microcontroller at step 320 initiates the reformation of the second capacitor followed by step 322, which is discussed below. If the self-discharge time is greater than approximately 5 seconds, then the microcontroller waits a second time period, e.g., approximately one week, at step 322, and then repeats the algorithm. As a result of the algorithm shown in FIG. 5 the first capacitor 268 and the second capacitor are reformed only after the microcontroller has determined, based on the self-discharge time for each capacitor, that the leakage current is high. Thus, the internal self-discharge rate of each capacitor is used to determine when the capacitor needs to be reformed.

Following reformation, the microcontroller 164 can invoke the electrode configuration switch 170 to drain the electrical charge from the first and second capacitors 268 and 272, respectively, without delivering electrical stimulation to the patient's heart 102. For example, the electrode configuration switch may include one or more shunt resistors that are used to drain the electrical charge from the capacitors without delivering electrical stimulation to the patient's heart following reformation. Alternatively, residual electrical charge that results from the reformation process may remain on the capacitors for an extended period of time.

Referring additionally to FIG. 6, in another algorithm 302 according to the present invention, the microcontroller 164 determines the "low-voltage" leakage current ("$I_L$") of a capacitor, i.e., either the first or second capacitor 268 or 272, respectively, and then determines whether the capacitor should be reformed based on the value of $I_L$. $I_L$ can be determined using several different techniques. For example, the microcontroller can determine $I_L$ by using the voltage measuring circuit 234 to measure the voltage, either $V_1$ or $V_2$, across the plates of the capacitor included in the apparatus 252 over a preselected time interval after the capacitor has been charged to an initial voltage. The microcontroller can then use a measured change in voltage ("$\Delta V$") over time to calculate $I_L$ occurring across the capacitor. In one specific example, $\Delta V$ following the charging of the capacitor to the initial voltage is measured over a one second interval, then $I_L$ is simply $\Delta V$ times the capacitance value of the capacitor.

The algorithm 302 shown in FIG. 6 starts at step 324. Next, at step 326, the microcontroller 164 determines the low-voltage $I_L$ for the capacitor, i.e., either the first capacitor or the second capacitor 268 or 272, respectively. The low-voltage $I_L$ is determined after the capacitor has been charged to a low voltage value, e.g., approximately 20 volts, and allowed to self-discharge. At step 328, the microcontroller determines if $I_L$ is greater than a predetermined current value, e.g., approximately 5 microamperes. If $I_L$ is not greater than approximately 5 microamperes, then the algorithm ends at step 330.

If $I_L$ is greater than 5 microamperes, then the microcontroller 164 initiates the application of a voltage to the capacitor 268 or 272 that is approximately equal to Vmax*[$I_L/(I_L+5$ microamperes)] at step 332, where Vmax is the maximum voltage rating for the capacitor, e.g., a voltage in a range from approximately 300 volts to approximately 700 volts. Thus, in this example algorithm 302, if $I_L$ is determined by the microcontroller to be 10 microamperes, then the capacitor will be charged to approximately two thirds of the maximum voltage rating for the capacitor. The larger $I_L$ is, the larger the capacitor's charging voltage value will be. Accordingly, the capacitor is reformed using a voltage that is mathematically determined based on $I_L$, and the voltage used for reforming the capacitor is positively correlated with the capacitor's $I_L$.

Next, at step 334, the microcontroller 164 applies the mathematically determined voltage to the capacitor 268 or 272 for a period of time from approximately one second to approximately 5 seconds, and the algorithm 302 is repeated. In particular, the microcontroller can apply the voltage to the capacitor for a period of time that is approximately equal to 5 seconds*[$I_L/(I_L+5$ microamperes)]. Thus, the voltage is applied to the capacitor for a period of time that is mathematically determined based on $I_L$.

Many other functions, e.g., linear and non-linear functions, can be used to optimize the charging characteristic of the capacitors 268 and 272 other than the mathematical functions included in FIG. 6. The functions would be determined to optimize the tradeoff between the energy used for reformation of the capacitors and the amount of degradation in the charging time that can be tolerated.

It is to be understood that if the microcontroller 164 detects the occurrence of a cardiac event that requires the IMD 100 to generate and deliver therapeutic electrical stimulation to the patient's heart 102 during any of the steps of the algorithms 300 and 302 according to the present invention, that the microcontroller will discontinued the algorithms and initiate a process for generating the therapeutic electrical stimulation. If this occurs, the algorithms and associated processes for reforming the capacitors will then be reset and/or delayed according to logic within the microcontroller.

Advantageously, the microcontroller 164 in embodiments of the present invention ascertains whether the leakage current for an IMD capacitor 268 or 272 exceeds a desired limit. If so, then a high voltage, e.g., from approximately 100 volts to approximately 700 volts, is used to reform the capacitor and reduce the leakage current through the capacitor's dielectric material. In this way, the IMD's microcontroller advantageously can reduce the amount of leakage current that occurs during the charging of the capacitor when therapeutic electrical stimulation is to be delivered to the patient's heart 102. This reduces the amount of electrical energy that must be provided from the IMD's battery 224 to the capacitors.

In addition, embodiments of the present invention provide for the capacitors 268 and 272 to be charged to a voltage value that is less than a maximum voltage rating depending upon the capacitor's value of leakage current. Because the amount of energy expended by the IMD's battery 224 during charging of the capacitor is proportional to the square of the voltage across the capacitor, charging the capacitor to a lower voltage results in a lower consumption of battery power so the IMD 100 is able to deliver therapeutic electrical stimulation to the patient's heart over a longer period of time. Thus, extending the IMD's life and providing for a potential reduction in the size of the battery. Also, by charging the capacitors to a voltage value that is less than the capacitor's maximum voltage rating, the capacitor is damaged less as a result of the charging process, thus, resulting in a longer lifetime for the capacitor.

Although the invention is described herein in conjunction with an IMD 100 having a microprocessor-based architecture, it will be understood that the IMD and the previously discussed algorithms 300 and 302 can be implemented using any logic-based, custom, integrated circuit architecture, if desired.

The foregoing detailed description of the present invention is provided for purposes of illustration, and it is not intended to be exhaustive or to limit the invention to the particular embodiments disclosed. The embodiments may provide different capabilities and benefits, depending on the configuration used to implement the key features of the invention. Accordingly, the scope of the invention is defined only by the following claims.

What is claimed is:

1. A method for determining when to reform a capacitor, the method comprising:
   a. charging the capacitor to a first voltage value;
   b. allowing the capacitor to self discharge;
   c. measuring a time it takes for the capacitor to self discharge to a second voltage value; and
   d. determining whether to reform the capacitor depending upon the measured self-discharge time.

2. The method according to claim 1, wherein the step of determining whether to reform the capacitor depending upon the measured self-discharge time includes:
   e. determining if the measured self-discharge time is greater than a first time period; and
   f. reforming the capacitor if the measured self-discharge time is not greater than the first time period.

3. The method according to claim 2, further comprising:
   g. waiting for a second time period if the measured discharge time is greater than the first time period; and
   h. repeating the steps of a-f.

4. The method according to claim 3, wherein:
   i. the first voltage value is approximately 20 volts;
   j. the second voltage value is approximately 10 volts;
   k. the first time period is approximately 5 seconds; and
   l. the second time period is approximately 1 week.

5. The method according to claim 2, further comprising:
   m. providing a second capacitor;
   n. charging the second capacitor to the first voltage value;
   o. allowing the second capacitor to self discharge;
   p. measuring a time it takes for the second capacitor to self discharge to the second voltage value;
   q. determining if the measured self-discharge time for the second capacitor is greater than the first time period; and
   r. reforming the second capacitor if the measured self-discharge time for the second capacitor is not greater than the first time period.

6. The method according to claim 5, further comprising:
   s. waiting for a second time period if the measured self-discharge time for the second capacitor is greater than the first time period; and
   t. repeating the steps of a-f and m-r.

7. A method for reforming a capacitor, the method comprising:
   a. determining a value of leakage current for the capacitor; and
   b. applying a voltage to the capacitor that has a value that is mathematically determined based on the value of the current;
   wherein the voltage that is applied to the capacitor has a value that is approximately equal to a maximum voltage rating for the capacitor multiplied by the value of the leakage current divided by the sum of the value of the leakage current and a predetermined current value.

8. The method according to claim 7, wherein:
   c. the maximum voltage rating for the capacitor is in a range from approximately 300 volts to approximately 700 volts; and
   d. the predetermined current value is approximately 5 microamperes.

9. The method according to claim 7, wherein the value of leakage current is determined mathematically based on a capacitance value of the capacitor, and a measured change in a value of voltage across the capacitor over a period of time.

10. The method according to claim 7, further comprising:
    e. determining if the value of leakage current is greater than a predetermined current value;
    f. ending the method before the step of applying the voltage to the capacitor if the value of leakage current is not greater than the predetermined current value; and
    g. performing the step of applying the voltage to the capacitor if the value of leakage current is greater than the predetermined current value.

11. The method according to claim 10, wherein the voltage is applied to the capacitor for a period of time that is mathematically determined based on the value of leakage current.

12. The method according to claim 11, wherein:
    h. the predetermined current value is 5 microamperes; and
    i. the period of time is selected from the group consisting of:
        i. a range from approximately 1 second to approximately 5 seconds, and
        ii. a value equal to 5 seconds multiplied by the value of leakage current and divided by the sum of the value of leakage current and the predetermined current value.

13. The method according to claim 11, further comprising repeating the steps of a-b and e-g.

* * * * *